US00PP21988P2

(12) United States Plant Patent
Giesen

(10) Patent No.: US PP21,988 P2
(45) Date of Patent: Jun. 21, 2011

(54) ***LOBELIA* PLANT NAMED 'TEC HEWHITT'**

(50) Latin Name: *Lobelia erinus*
Varietal Denomination: Tec Hewhitt

(75) Inventor: Eric Giesen, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 12 days.

(21) Appl. No.: 12/657,389

(22) Filed: Jan. 20, 2010

(51) Int. Cl.
*A01H 5/00* (2006.01)

(52) U.S. Cl. ..... Plt./451

(58) Field of Classification Search ..... Plt./451
See application file for complete search history.

(56) References Cited

U.S. PATENT DOCUMENTS

| | | | | |
|---|---|---|---|---|
| PP18,216 | P2 * | 11/2007 | van Kleinwee | Plt./451 |
| PP19,693 | P2 * | 2/2009 | Klemm | Plt./451 |
| PP21,128 | P2 * | 6/2010 | Klemm et al. | Plt./451 |

OTHER PUBLICATIONS

UPOV ROM GTITM Computer Database, GTI Jouve Retrieval Software Mar. 2010.*

* cited by examiner

*Primary Examiner* — Wendy C Haas
(74) *Attorney, Agent, or Firm* — S. Matthew Edwards

(57) ABSTRACT

A new *Lobelia* plant named 'Tec Hewhitt' particularly distinguished by the large pure white flowers, medium green foliage, vigorous and well branched habit, and early flowering.

1 Drawing Sheet

Latin name of the genus and species of the plant claimed: *Lobelia erinus.*

Varietal denomination: 'Tec Hewhitt'.

BACKGROUND OF THE NEW PLANT

The present invention comprises a new *Lobelia*, botanically known as *Lobelia erinus*, and hereinafter referred to by the variety name 'Tec Hewhitt.'

'Tec Hewhitt' is a product of a planned breeding program. The new cultivar has large pure white flowers, medium green foliage, vigorous and well branched habit, and early flowering.

'Tec Hewhitt' originated from a hybridization made in July 2006 in a controlled breeding environment in Andijk, Netherlands. The seed was sown in September 2006. The female parent was the unpatented, proprietary plant designated 'LOB03-116-1,' with smaller white flowers, lighter foliage and shorter stems.

The male parent of 'Tec Hewhitt' was an unpatented, proprietary plant designated as 'LOB02-21-1' with white flowers. 'LOB02-21-1' has smaller foliage, longer internodes, thinker stems, and a less trailing habit than 'Tec Hewhitt.'

'Tec Hewhitt' was selected as one flowering plant within the progeny of the stated cross in the January 2007 in a controlled environment in Andijk, Netherlands.

The first act of asexual reproduction of 'Tec Hewhitt' was accomplished when vegetative cuttings were propagated from the initial selection in January 2007 in a controlled environment in Andijk, Netherlands.

BRIEF SUMMARY OF INVENTION

Horticultural examination of plants grown from cuttings of the plant initiated in January 2007, and continuing thereafter, has demonstrated that the combination of characteristics as herein disclosed for 'Tec Hewhitt' are firmly fixed and are retained through successive generations of asexual reproduction.

'Tec Hewhitt' has not been observed under all possible environmental conditions. The phenotype may vary significantly with variations in environment such as temperature, light intensity and day length.

A Plant Breeder's Right for this cultivar was applied for in Canada on Jan. 30, 2009. 'Tec Hewhitt' has not been made publicly available more than one year prior to the filing of this application.

The following traits have been repeatedly observed and are determined to be basic characteristics of the new variety. The combination of these characteristics distinguishes this *Lobelia* as a new and distinct variety.

BRIEF DESCRIPTION OF THE PHOTOGRAPHS

The accompanying photographic drawing shows typical flower and foliage characteristics of 'Tec Hewhitt' with colors being as true as possible with an illustration of this type.

Figure 1:
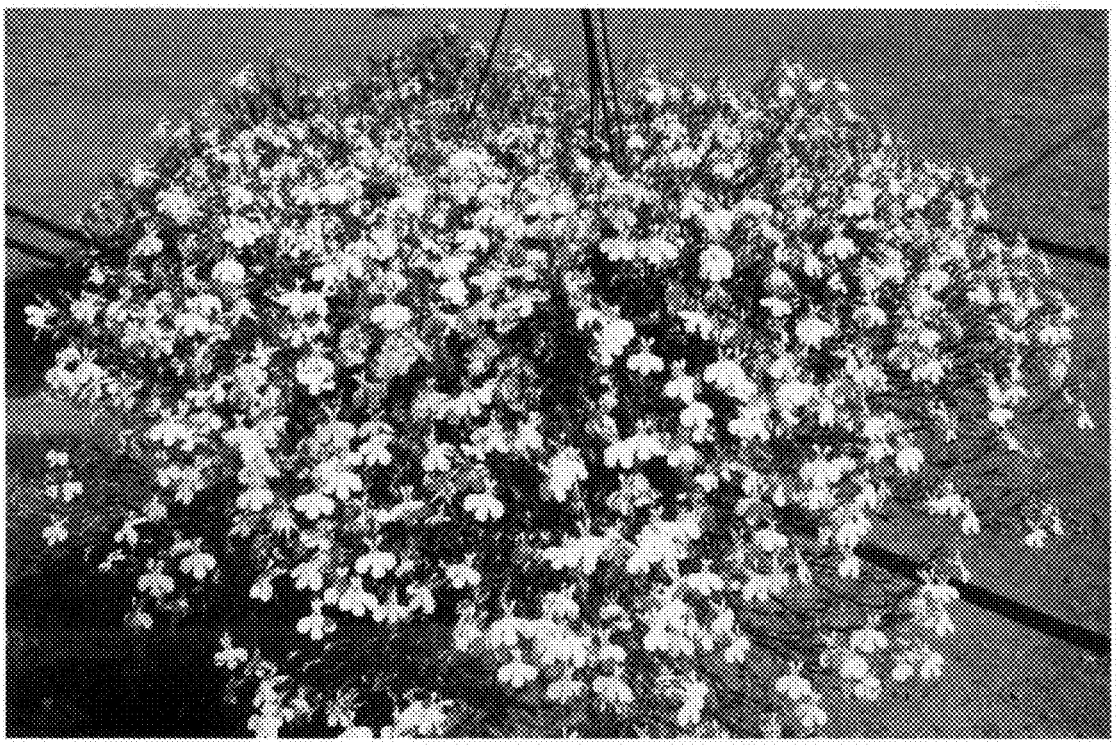
Figure 2:
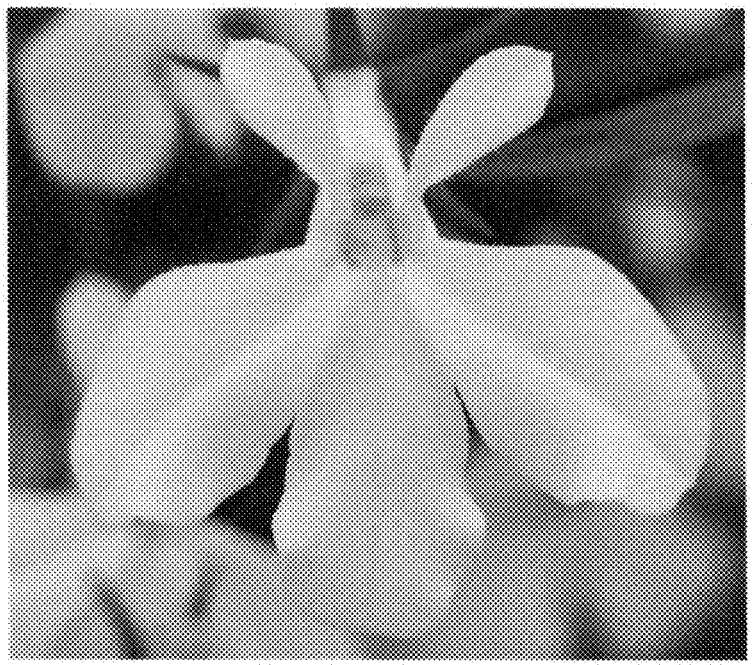

The photographic drawing shows in FIG. 1 three flowering potted plants of the new variety, and in FIG. 2 a close-up of the flowers.

DETAILED BOTANICAL DESCRIPTION

The plant descriptions and measurements were taken in Hillscheid, Germany in April 2009. These plants were approximately 11 weeks old and were growing in 12 cm pots, in greenhouse trials. The plants used for the photographs were about 12-14 weeks old and growing in Gilroy, Calif.; three plants in a 10 inch basket.

Color references are made to The Royal Horticultural Society Colour Chart (R.H.S.) 2001.

TABLE 1

DIFFERENCES BETWEEN THE NEW VARIETY 'TEC HEWHITT' AND A SIMILAR VARIETY

| | 'Tech Hewhitt' | 'Lobtrawi' (U.S. Plant Pat. No. 18,216) |
|---|---|---|
| Flower size: | Larger | Smaller |
| Foliage size: | Larger | Smaller |
| Stem diameter: | Wider/thicker | Narrower/thinner |
| Plant habit: | More trailing | Less trailing |

Plant:

*Form, growth and habit.*—Vigorous growth habit; dense and freely branched with medium long internodes, initially low spreading becoming trailing.

*Plant height.*—5-6 cm.

*Plant height* (*inflorescence included*).—8-10 cm.

*Plant width.*—About 50 cm.

*Garden performance and tolerance to weather.*—Good.

*Crop time to flowering.*—About 10 weeks.

Roots:

*Number of days to initiate roots and develop roots.*—21-24 days at about 22 degrees C.

*Type.*—Fine, fibrous, free branching.

*Color.*—RHS N155B but whiter.

Foliage:

*Arrangement.*—Alternate.

*Immature, leaf color, upper surface.*—RHS 137B to RHS 137C.

*Lower surface.*—RHS 138B.

*Mature, leaf color, upper surface.*—RHS 137B to RHS 137C.

*Lower surface.*—RHS 137B.

*Length.*—4.0-5.0 cm.

*Width.*—0.9-1.2 cm.

*Shape.*—Elliptical to spatulate.

*Base shape.*—Attenuate to cuneate.

*Apex shape.*—Acute.

*Margin.*—Weakly dentate.

*Texture, upper surface.*—Glabrous and slightly glossy.

*Lower surface.*—Glabrous and slightly glossy.

*Color of veins, upper surface.*—Indistinct.

*Color of veins, lower surface.*—RHS 138A.

Stem:

*Quantity of main branches per plant.*—10-15.

*Color of stem.*—RHS 137A to RHS 137B.

*Length of stem.*—10-15 cm.

*Diameter.*—0.2-0.3 cm.

*Length of internodes.*—1.0-2.0 cm.

*Texture.*—Glabrous, sparsely hirsute.

Inflorescence:

*Type.*—Raceme, terminal (at stem end), composed of single flowers in an alternate arrangement, with one flower per node, subtended by a narrow leaflet.

*Blooming habit.*—Continuous through the growing season.

*Quantity of inflorescences per plant.*—20-30.

*Quantity of flowers per stem.*—About 3-5 open flowers with 10-16 buds.

*Lastingness of individual blooms on the plant.*—5-7 days depending on temperature.

*Fragrance.*—None.

*Color of peduncle.*—RHS 137A.

*Length of peduncle.*—13-17 cm.

*Peduncle diameter.*—0.2 cm.

*Texture.*—Glabrous, glossy.

*Color of pedicels.*—RHS 137C.

*Length of pedicels.*—About 1.8-2.1 cm.

*Diameter of pedicels.*—0.1 cm.

*Texture.*—Glabrous.

Bud (just before opening/showing color):

*Color.*—RHS 154D.

*Length.*—1.3-1.5 cm.

*Width.*—0.4-0.5 cm.

*Shape.*—Oblong.

Flower:

*Corolla type.*—Single, zygomorphic; upper lip has two small lobes and lower lip has three larger and broader lobes; lobes are fused at the base.

*Main color upper and lower petals, upper surface.*—RHS 155D but whiter.

*Markings on lower lip.*—No markings usually, under certain conditions margins may be slightly bluish infused.

*Nectar guide.*—At the base (inner end) of the lower lip, 2 small, dots of RHS 144B, and fine lines running into the funnel.

*Color upper and lower petals, lower surface.*—RHS 155D.

*Flower diameter, length.*—2.5 cm.

*Flower, width.*—2.7 cm.

*Corolla tube length.*—1.1-1.2 cm.

*Tube width.*—0.4 cm.

Petal (lobes):

*Apex.*—Upper petals acute; lower petals rounded to weakly mucronulate.

*Base.*—Fused.

*Margin.*—Entire.

*Texture.*—Both surfaces partly glabrous, edges of upper petals ciliate, and short hair along the veins of the lower petals, and on the funnel surface.

*Upper petals, length* (*from the corolla opening*).—0.7-0.8 cm.

*Upper petals, width.*—0.3 cm.

*Lower petals, length* (*from the corolla opening*).—1.3-1.4 cm.

*Lower petals, width.*—0.7-0.9 cm.

Calyx:

*Quantity and form.*—5 sepals in a whorl, fused at the base and somewhat funnel shaped.

*Color, upper surface.*—RHS 137A to RHS 137B with RHS 139A at the apices.

*Lower surface.*—RHS 137A to RHS 137B with RHS 139A at the apices.

*Length.*—1.3 cm.

*Width.*—0.1 cm.

*Shape.*—Ligulate (free ends).

*Apex shape.*—Sharply acute.

*Based.*—Fused.

*Margins.*—Entire.

*Texture, upper surface.*—Hirsute basally; glossy and glabrous otherwise.

*Lower surface.*—Hirsute basally; glossy and glabrous otherwise.

Reproductive organs:

*Pistil.*—1.

*Length.*—1.4 cm.

*Style color.*—RHS 145B.

*Style length.*—1.2 cm.

*Stigma color.*—Between RHS 79D and RHS 86D.

*Stamens.*—5.
*Color of filaments.*—Lighter than RHS 155D.
*Length filaments.*—0.7-0.9 cm.
*Anther color.*—RHS 197A.
*Anther length.*—0.2-0.3 cm.
*Color of pollen.*—RHS 8B.
*Pollen amount.*—Sparse.
*Fertility/seed set.*—Has not been observed on this hybrid.

Disease/pest resistance: Has not been observed on this hybrid.

What is claimed is:

1. A new and distinct variety of *Lobelia* plant named 'Tec Hewhitt,' substantially as illustrated and described herein.

* * * * *

UNITED STATES PATENT AND TRADEMARK OFFICE

CERTIFICATE OF CORRECTION

PATENT NO. : PP21,988 P2
APPLICATION NO. : 12/657389
DATED : June 21, 2011
INVENTOR(S) : Giesen It is certified that error appears in the above-identified patent and that said Letters Patent is hereby corrected as shown below:

IN THE SPECIFICATIONS:

At column 1, line 23, please delete “thinker” and insert therefor --thinner--

Signed and Sealed this
Second Day of August, 2011

David J. Kappos

David J. Kappos
*Director of the United States Patent and Trademark Office*